United States Patent
Schweizer

(10) Patent No.: US 9,962,138 B2
(45) Date of Patent: May 8, 2018

(54) DEVICE AND METHOD FOR DYNAMICALLY STORING MEDICAL DEVICE POSITIONS, BIOMEDICAL ENGINEERING IMAGING SYSTEM, AND COMPUTER PROGRAM PRODUCT

(71) Applicant: SIEMENS AKTIENGESELLSCHAFT, Munich (DE)

(72) Inventor: Hans Schweizer, Plattling (DE)

(73) Assignee: Siemens Aktiengesellschaft, Munich (DE)

( * ) Notice: Subject to any disclaimer, the term of this patent is extended or adjusted under 35 U.S.C. 154(b) by 158 days.

(21) Appl. No.: 15/046,897

(22) Filed: Feb. 18, 2016

(65) Prior Publication Data
US 2016/0235386 A1   Aug. 18, 2016

(30) Foreign Application Priority Data
Feb. 18, 2015 (DE) .................. 10 2015 202 911

(51) Int. Cl.
*A61B 6/00*   (2006.01)

(52) U.S. Cl.
CPC ............. *A61B 6/54* (2013.01); *A61B 6/4441* (2013.01); *A61B 6/4476* (2013.01); *A61B 6/465* (2013.01); *A61B 6/467* (2013.01); *A61B 6/547* (2013.01)

(58) Field of Classification Search
CPC ......... A61B 6/00; A61B 6/4441; A61B 6/465; A61B 6/467; A61B 6/54; A61B 6/46; A61B 6/461; A61B 6/462; A61B 6/464; A61B 6/547; A61B 6/587; G06F 19/3406

USPC .................. 378/98.5, 114, 115, 205
See application file for complete search history.

(56) References Cited

U.S. PATENT DOCUMENTS

| | | | |
|---|---|---|---|
| 7,937,163 | B2 | 5/2011 | Sekiguchi |
| 2002/0039403 | A1 | 4/2002 | Oota |
| 2011/0305320 | A1 | 12/2011 | Suuronen et al. |
| 2013/0243160 | A1 | 9/2013 | Graumann et al. |

FOREIGN PATENT DOCUMENTS

| | | |
|---|---|---|
| CN | 201681599 U | 12/2010 |
| CN | 102309334 A | 1/2012 |
| DE | 102012204018 A1 | 9/2013 |
| WO | 2014057385 A2 | 4/2014 |

*Primary Examiner* — Jurie Yun
(74) *Attorney, Agent, or Firm* — Laurence Greenberg; Werner Stemer; Ralph Locher

(57) ABSTRACT

A storage apparatus for dynamically storing and for recalling a position of an imaging biomedical engineering device has an interface to a position establishment apparatus of the imaging biomedical engineering device. A display unit has a display field with a user interface having a selectable number of virtual storage buttons that are actuatable by a pointer object. If an unoccupied virtual storage button which does not yet have a medical device position assigned thereto is actuated, the storage button is assigned a current medical device position. If an occupied virtual storage button which already has a medical device position assigned thereto is actuated, the stored medical device position is selected and visualized on the display field. A biomedical engineering imaging system as well as a method for dynamically storing and for recalling medical device positions and a program product are described.

16 Claims, 3 Drawing Sheets

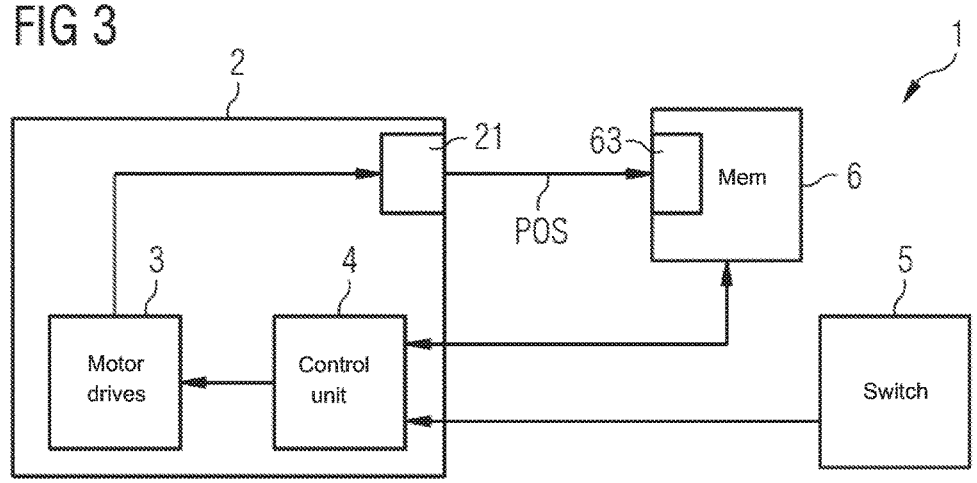
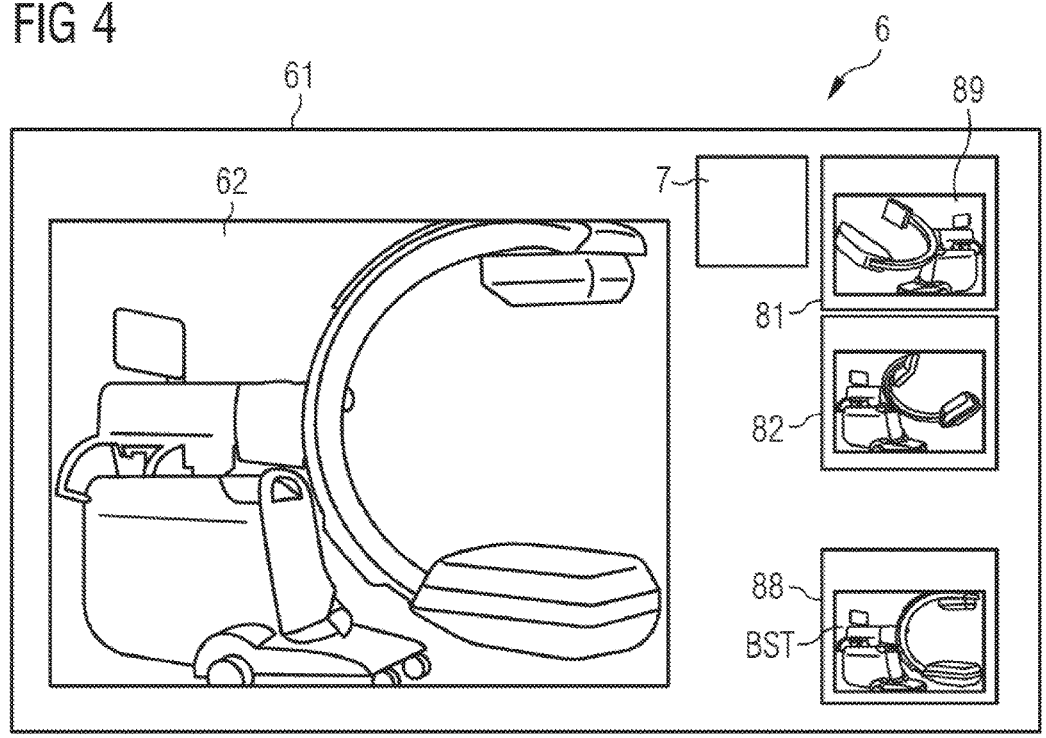

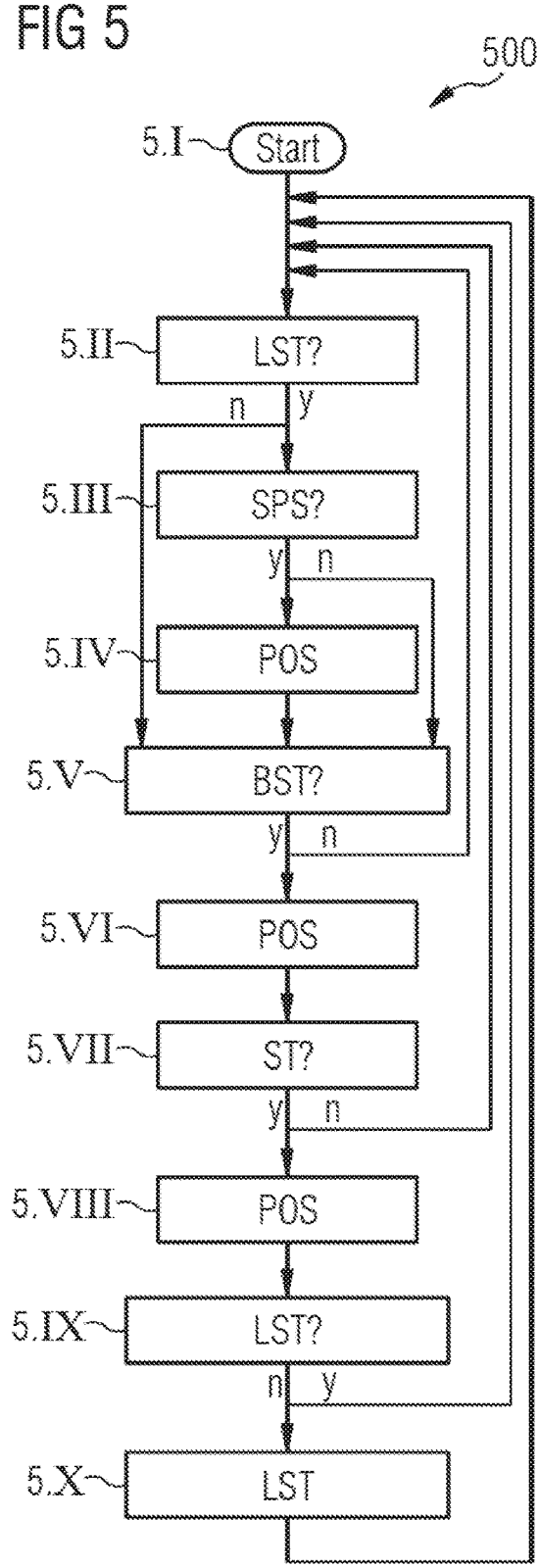

DEVICE AND METHOD FOR DYNAMICALLY STORING MEDICAL DEVICE POSITIONS, BIOMEDICAL ENGINEERING IMAGING SYSTEM, AND COMPUTER PROGRAM PRODUCT

CROSS-REFERENCE TO RELATED APPLICATION

This application claims the priority, under 35 U.S.C. § 119, of German patent application DE 10 2015 202 911.5, filed Feb. 18, 2015; the prior application is herewith incorporated by reference in its entirety.

BACKGROUND OF THE INVENTION

Field of the Invention

The invention relates to an apparatus for dynamically storing and recalling medical device positions. Moreover, the invention relates to a biomedical engineering imaging apparatus. Furthermore, the invention relates to a method for dynamically storing and for recalling medical device positions.

Many imaging biomedical engineering devices, such as C-arm devices or radiography installations or fluoroscopy installations can be moved by motor in respect of a plurality of axes. In numerous work procedures, it is desirable to store device positions and to recall the device position during the later course of the medical treatment, for example for positioning an implant in the case of a surgical intervention, in order to be able to carry out a renewed image recording at the same position. Conventionally, the desired position is not visualized, or only visualized in outlines, when recalling the device position such that, when subsequently recalling the stored position, it is not that easy to identify the specific position to which the biomedical engineering device is in fact moved. Conventionally, it is difficult to find the correct device position, particularly if a plurality of different device positions are stored. In conventional systems, a set number of storage buttons is usually present in order to be able to store a specific small number of device positions in a manner assigned to the respective storage button and recall said positions in order to be able to drive the system to the stored position. This harbors disadvantages if the number of device positions to be stored is increased beyond the number of buttons. Furthermore, as already mentioned, it is usually difficult in conventional storage apparatuses to immediately find the button with the desired stored device position when recalling a specific device position.

SUMMARY OF THE INVENTION

It is accordingly an object of the invention to provide an apparatus and a method which overcome the above-mentioned and other disadvantages of the heretofore-known devices and methods of this general type and which provide for a storage apparatus for storing and recalling device positions during the run-time of the imaging device which, compared to conventional arrangements, is more flexible and enables a simplified operation.

With the foregoing and other objects in view there is provided, in accordance with the invention, a storage apparatus for dynamically storing and recalling a position of an imaging biomedical engineering device, the storage apparatus comprising:

an interface to a position establishment apparatus of the imaging biomedical engineering device, configured to receive position data from the position establishment apparatus;

a display unit with a display field, having a user interface with a selectable number of virtual storage buttons which are actuatable by way of a pointer object;

wherein the storage apparatus is configured as follows:

if an unoccupied virtual storage button which does not yet have a medical device position assigned thereto is actuated, the given storage button is assigned a current medical device position, representing a current position of the biomedical engineering device; and if an occupied virtual storage button which already has a medical device position assigned thereto is actuated, the stored medical device position is selected and visualized on the display field.

In other words, the storage apparatus according to the invention for dynamically storing a position of an imaging biomedical engineering device comprises an interface to a position establishment apparatus of the imaging biomedical engineering device. The interface is configured to receive position data from the position establishment apparatus. Furthermore, the storage apparatus comprises a display unit with a display field with a user interface which comprises a selectable number of virtual storage buttons. Here, the virtual storage buttons are actuatable by means of a pointer object. The storage apparatus is configured in such a way that, if an unoccupied virtual storage button which does not yet have a medical device position assigned thereto is actuated, this storage button is assigned a current medical device position, in which the biomedical engineering device currently is, and, if an occupied virtual storage button which already has a medical device position assigned thereto is actuated, the stored medical device position is selected and visualized on the display field.

A virtual storage button should be understood to mean that the storage button is not physically present but only displayed on the screen. In this manner, the number of virtual storage buttons can be adapted to the current requirement in each case. Furthermore, a virtual storage button can complete the same tasks as a physical storage button. In particular, it can be actuated, for example, with the aid of a pointer object, such as e.g. a finger of a user if the display is a touchscreen or with the aid of a stylus or mouse pointer.

An unoccupied virtual storage button should be understood to mean a virtual storage button in respect of which no device position has yet been stored in an assigned manner.

By contrast, an occupied virtual storage button should be understood to mean a virtual storage button in respect of which a device position has already been stored in an assigned manner.

The biomedical engineering imaging system according to the invention has an adjustable image-recording unit and the storage apparatus according to the invention. By way of example, the adjustable image-recording unit can be a C-arm device, the C-arm of which is rotatably adjustable in respect of a plurality of axes.

In the method according to the invention for dynamically storing medical device positions in a storage apparatus with a display unit with a display field with a user interface, which comprises a selectable number of virtual storage buttons, a current medical device position is stored in a manner assigned to the actuated storage button if an unoccupied virtual storage button which does not yet have a medical device position assigned thereto is actuated and, if an occupied virtual storage button which already has a medical device position assigned thereto is actuated, the stored medical device position is selected and visualized on the display field.

A computer program is also claimed, which is loadable directly into a storage of a programmable storage apparatus according to the invention, with program code sections for carrying out all steps of the method according to the invention when the program is executed in the storage apparatus.

Further advantageous embodiments and developments of the invention emerge from the further dependent claims and the description below. Here, the method according to the invention for dynamically storing and for recalling medical device positions can also be developed in a manner analogous to the dependent method claims.

Particularly preferably, the storage apparatus according to the invention is configured in such a way that a screenshot of the respectively stored medical device position is displayed on the occupied virtual storage buttons. Here, the screenshot is imaged in accordance with a fully synchronous 3D model of the installation and in accordance with the real medical device position.

The imaging on the occupied storage buttons makes the correct selection of the virtual storage button with the desired device position easier. By way of example, the storage apparatus internally generates a 3D model (similar to a 3D CAD model) of the mechanism of the medical device, including a depiction, synchronous with reality, of all dynamically movable axes. This freely rotatable and zoomable 3D model, which exactly reproduces the mechanical conditions of the system at all times, is used to generate 2D screenshots when a position is stored. This screenshot is placed on the storage button assigned in each case.

In a particularly effective variant of the storage apparatus according to the invention, there is dynamic recording of screenshots for the purpose of device position visualization and filing of the screenshots on the storage button in each case. Expressed differently, the device positions are detected and stored at different times during the operation of the biomedical engineering device such that these can be driven to again at any time.

In a particularly useful embodiment of the storage apparatus according to the invention, a 3D model is generated with the aid of an image recording from a 3D camera. In the image recording, real volume data, including the user position, are also recorded and included when creating the 3D model.

Additionally, when creating the 3D model, the calculated 3D model can also automatically be rotated in such a way if the user is identified by the camera that the screenshot is generated from exactly the same perspective/direction of view on the system as the one with which the user currently sees the system. By way of example, if the user is to the right of the C-arm device, the whole C-arm model is rotated and stored on the screenshot in such a way that it looks the same as for a user standing to the right of the C-arm.

Moreover, the user interface can comprise a virtual delete button that is actuatable by means of a pointer object, to be precise in such a way that a storage button is dragged by the pointer object to the delete button and dropped there, with the medical device position assigned to this storage button being deleted and the screenshot being removed.

In one embodiment of the storage apparatus according to the invention, the user interface has an additional virtual storage command button. Furthermore, the storage apparatus is configured in such a way that a current medical device position is only stored if the storage command button is also actuated in addition to the empty virtual storage button. In this embodiment, the actuation of the virtual storage button merely has a selection function. By contrast, the process of storing a device position is triggered by actuating an additional command button. In this manner, inadvertent storing of a device position is prevented.

In a particularly practical embodiment of the storage apparatus according to the invention, the storage apparatus has an additional switch, the actuation of which after selecting an occupied virtual storage button with a stored medical device position generates a control command for setting a medical device in accordance with the selected stored medical device position. This switch can be part of the storage apparatus, but also a separate input device such as e.g. a foot switch.

In an alternative embodiment of the storage apparatus according to the invention, the virtual storage buttons have a selection function and, additionally, a storage function or a control function for controlling the setting of a medical device position, depending on the actuation time.

By way of example, the selection function of a virtual storage button is triggered in the case of a short actuation of the virtual storage button and the storage function or the control function is triggered in the case of a relatively long actuation of the virtual storage button.

Expressed differently, the virtual storage buttons are selected in the case of a brief actuation and they exert a storage function or a control function in the case of a longer term actuation. By way of example, if an unoccupied virtual storage button is actuated briefly in this variant, it is selected for storing a device position. If it is subsequently actuated over a relatively long period of time, the device position is stored in a manner assigned to the selected virtual storage button. If, furthermore, an occupied virtual storage button is actuated briefly, this occupied virtual storage button is selected and the device position assigned to the selected virtual storage button is visualized. If the same button is subsequently actuated for a relatively long period of time, the biomedical engineering imaging apparatus is driven into the device position assigned to the selected virtual storage button.

In a preferred embodiment of the storage apparatus according to the invention, device positions predefined in advance are stored in a manner assigned to some of the virtual storage buttons. Here, the predefined device positions may comprise a transport position and a zero-point position. Due to the dynamic implementation of the virtual storage buttons, there is no capacity conflict between the storage buttons reserved for the pre-setting and the remaining storage buttons either.

Preferably, the biomedical engineering imaging system according to the invention has an additional setting switch, which, after selecting an occupied virtual storage button and additionally actuating the additional setting switch, is configured to output a control signal for setting the medical device position assigned to the occupied virtual storage button. By way of example, the additional setting switch has a hand switch or a foot switch, which is configured to output a control signal only during the period of actuation of the setting switch.

Furthermore, the biomedical engineering imaging system can comprise a C-arm system.

In the case of a C-arm system, the stored and visualized medical device position can comprise a spatial orientation of the C-arm of the C-arm system. Furthermore, the stored and visualized medical device position can comprise a relative position of the biomedical engineering imaging system, for example a C-arm system, in relation to a patient.

Additionally, the relative position in respect of the user can also be detected using an image recording apparatus, such as e.g. a camera, so that the model on the display is rotated in such a way that it corresponds to the field of view of the operating staff, significantly improving the recognition value of the screenshot and hence the user-friendliness.

The biomedical engineering imaging system can additionally have a 3D camera configured to record real volume data including the user position, which are taken into account when creating the 3D model.

Other features which are considered as characteristic for the invention are set forth in the appended claims.

Although the invention is illustrated and described herein as embodied in a dynamic storing of medical device positions, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 3 shows a block diagram of a biomedical engineering imaging apparatus with a storage apparatus in accordance with an exemplary embodiment of the invention;

FIG. 4 shows a schematic illustration of a display unit of a storage apparatus in accordance with one exemplary embodiment of the invention; and FIG. 5 is a flowchart illustrating an exemplary embodiment of the method according to the invention for dynamically storing and for recalling medical device positions.

DETAILED DESCRIPTION OF THE INVENTION

Figure 1:
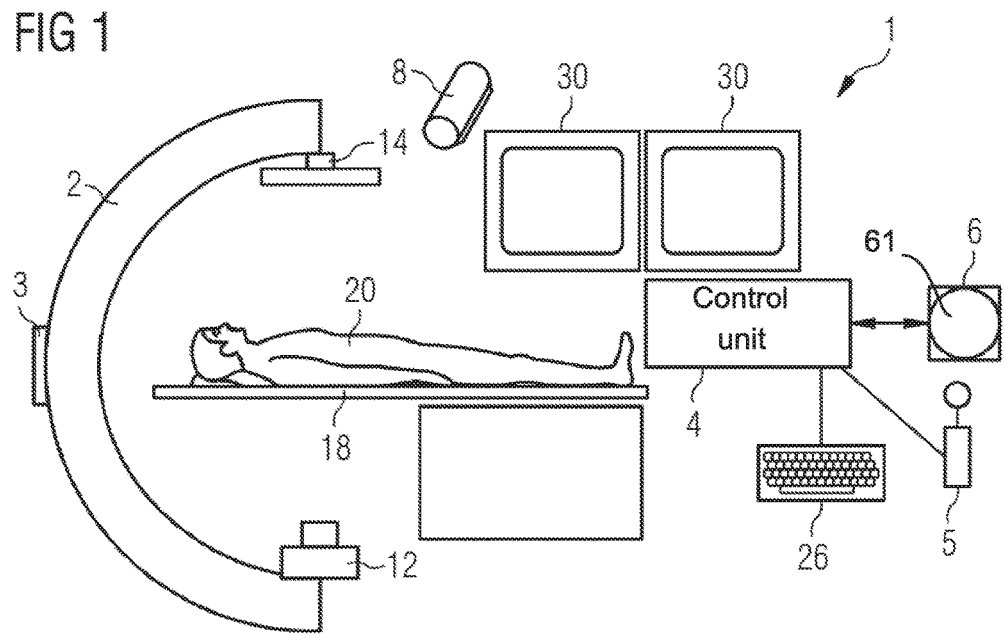
FIG. 1 shows a schematic illustration of a C-arm system in accordance with one exemplary embodiment of the invention.

Referring now to the figures of the drawing in detail and first, particularly, to FIG. 1 thereof, there is schematically depicted an imaging biomedical engineering system 1, which is a C-arm system in this specific exemplary embodiment, with a storage apparatus 6 according to the invention. The C-arm system 1 comprises an x-ray C-arm 2, which is rotatable as a whole and tiltable about the axis of rotation thereof. The x-ray C-arm 2 supports an x-ray radiation source 12 and an x-ray radiation detector 14. The x-ray C-arm 2 can be rotated about various axes and it is also horizontally displaceable with the aid of motors 3 (while FIG. 1 only shows one motor, such an arrangement usually has a multiplicity of motors for rotation about various axes or for realizing translational movements).

Figure 2:
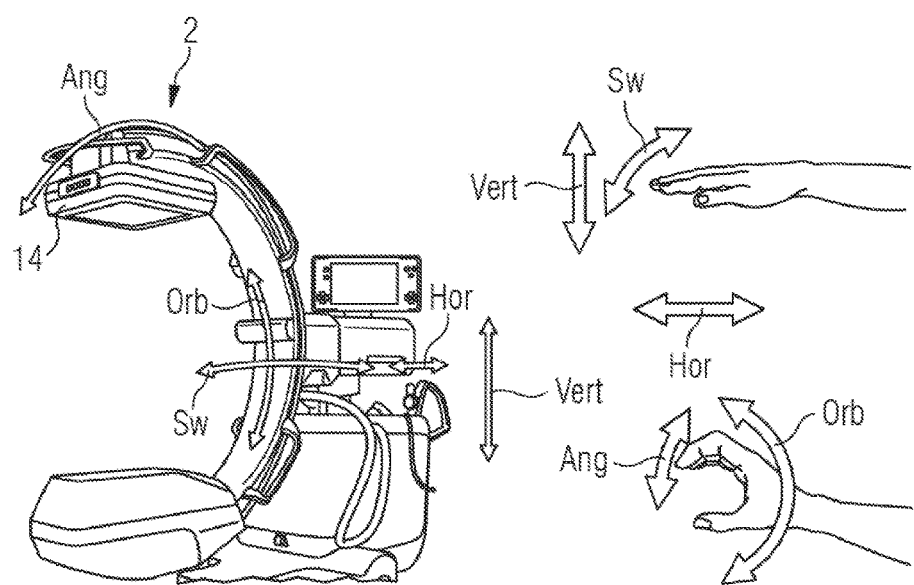
FIG. 2 is a schematic illustration of various adjustment possibilities of a C-arm system.

FIG. 2 shows a typical C-arm device 2 which has various degrees of freedom, in respect of which its position and orientation are modifiable. The different degrees of freedom are symbolized by arrows to the right of the image. The device 2 shown in FIG. 2 can be adjusted in the vertical direction Vert. Moreover, it can be pivoted about the vertical axis, denoted by Sw in FIG. 2. Furthermore, the device 2 can be displaced in the horizontal direction Hor. Moreover, an orbital rotation Orb of the C-arm is possible. Additionally, the entire C-arm of the device 2 can be rotated in an angular manner, denoted by Ang in FIG. 2. That is to say, both the detector and the radiation generator on the opposite side of the detector also move when the C-arm is rotated.

A patient 20 on a patient table 18 is shown in FIG. 1. The C-arm system 1 furthermore comprises a control unit 4 or controller 4, for short, which is operable by way of input means 26, 5. By way of example, a keyboard 26 and an operating switch 5, which is embodied as a dead man's switch and which serves to set a specific position of the C-arm device 2, are shown as input means. Additionally, the C-arm system 1 can also have a touchscreen 61 for operating the system. Furthermore, the C-arm system 1 comprises a plurality of screens 30, on which recorded x-ray images can be displayed. In the embodiment shown in FIG. 1, the above-described touchscreen 61 is part of a storage apparatus 6 of the C-arm system 1. The storage apparatus 6 serves to store and visualize recording positions POS of the C-arm device 2, at which recording of the image was carried out. If one of the positions of the C-arm device 2 stored in the storage apparatus 6 is selected, this position is forwarded to the control unit 4. If the operating switch 5, by means of which the position of the C-arm device 2 can be modified, is now actuated, the position of the C-arm device 2 received by the control unit 4 is automatically driven to. A 3D model of the C-arm system 1 is also calculated using the storage apparatus 6 and corresponding screenshots for storage buttons displayed on the touchscreen 61 are generated dynamically in accordance with the 3D model. Use can also be made of a 3D camera 8 for recording the 3D position of the device and of the patient.

FIG. 3 schematically shows, with the aid of a block diagram, an imaging biomedical engineering system 1 in accordance with one exemplary embodiment of the invention. The imaging biomedical engineering system 1, for example a C-arm system, has an imaging biomedical engineering device 2 comprising a plurality of movable axes, as is the case for the C-arm device in FIGS. 1 and 2. Sensors (not shown here) are assigned to the individual axes and these generate information in respect of the current position of the biomedical engineering device. Data POS in respect of the current device position are established on the basis of the established information. Additionally, a 3D camera 8 (see FIG. 1) which likewise detects position data and transmits it to the storage apparatus 6 can also be connected to the system 1. Subsequently, the established position information POS is transferred to a storage apparatus 6 in accordance with one exemplary embodiment of the invention. The biomedical engineering device 2 furthermore also comprises motor-driven drives 3 for setting a specific position of the biomedical engineering device 2 and a control unit 4, by means of which the motor-driven drive 3 and possibly further units for controlling the biomedical engineering device 2 are controllable. The storage apparatus 6 has an interface 63 which connects to a position establishment apparatus 21 of the imaging biomedical engineering device 2 and is configured to receive position data from the position establishment apparatus 21. The storage apparatus 6 comprises a monitor which, for example, is embodied as a touchscreen. Virtual buttons (see FIG. 4), to which dynamically occupyable storage places for storing device positions are assigned, are arranged on the touchscreen 61 and said buttons can be actuated with the aid of a pointer object such as e.g. a finger of a user. If one of the occupied storage buttons is pressed at this time, the device position assigned to this occupied storage button is displayed on the touchscreen and forwarded to the controller or control unit 4. By way of example, if an additional operating switch 5, which e.g. is embodied as a type of release switch, is subsequently actuated, the biomedical engineering device 2 is automatically moved into the position stored in the control unit 4. In this case, the operating switch 5 serves to ensure the presence of the operating staff while driving into a selected device position. The operating switch can also be omitted if the employed touchscreen is embodied in such a way that it continues to ensure non-falsified user inputs in the first error case. In this case, driving to the position can also be carried out by continuous pressure on the virtual storage button.

However, the actual control of driving to the selected device position is carried out in an automated manner on the basis of the device position stored in the control unit 4. Targeted control of the biomedical engineering device 2 by the operating staff is therefore not required in this arrangement in accordance with one exemplary embodiment of the invention.

FIG. 4 once again shows in detail a variant of the storage apparatus 6 in accordance with one exemplary embodiment of the invention. The storage apparatus 6 comprises a touchscreen 61 with a user interface which, in the left-hand region, has a display field 62 for visualizing a biomedical engineering device 2 in a specific device position. Additionally, the user interface has a plurality of virtual storage buttons 81, 82, 88, which serve for storing positions POS of the biomedical engineering device 2 assigned to the individual storage buttons and being able to recall these in a targeted manner. To this end, the virtual storage buttons each have a small storage button display field 89, on which the respectively stored device position, which was generated dynamically as a screenshot from a 3D model during storage, is schematically displayed so that it is easier to recall a specific stored device position by actuating the respective storage button 81, 82, 88. As already mentioned previously, when a specific device position is recalled, said device position is transmitted to the control unit 4 (see FIG. 3). As an alternative to actuating a hand switch 5 for driving to the recalled device position, this driving can also be triggered by continuous pressure on, or actuation of, the selected virtual storage button which is assigned the recalled device position. The user interface of the storage apparatus 6 moreover comprises a virtual storage command button 7, which serves to trigger storing of a current medical device position if the virtual storage command button 7 is pressed in addition to a still unoccupied virtual storage button LST. In this variant, the actuation of a virtual storage button 81, 82, 88 therefore only serves to select the respective storage button. Here, a specific device position is always only stored once the virtual storage command button 7 has also been pressed. Furthermore, the storage apparatus 6 shown in FIG. 4 can also comprise a delete button (not shown here). By way of example, the latter can be configured in such a way that a storage button is dragged to this button by a finger or a pointer device (as when files are pushed into the recycle bin in the case of Windows) and dropped there. Thus, the position in this storage button is deleted and the screenshot is removed.

FIG. 5 elucidates in a flowchart a method 500 for dynamically storing and recalling medical device positions in accordance with an exemplary embodiment of the invention. The method 500 is started in step 5.I; by way of example, this can be brought about by switching the storage apparatus 6 on. By way of example, there are a predetermined number of virtual storage buttons at the start, of which at least one is still "empty", i.e. not occupied. What is determined in step 5.II is whether an unoccupied "empty" virtual storage button LST was pressed in an actuating manner. If this is the case, which is denoted by "y" in FIG. 5, there is a query in step 5.III as to whether a storage command SPS was triggered, for example by actuating an additional storage command button 7. However, if no occupied "empty" virtual storage button LST was actuated in step 5.II, which is denoted by "n" in FIG. 5, there is a transition to step 5.V. If it is established in step 5.III that a storage command SPS was triggered, which is denoted by "y" in FIG. 5, there is a transition to step 5.IV. In step 5.IV, a current medical device position POS is stored, and a screenshot is generated from the fully synchronous 3D model of the installation and said screenshot is placed onto the storage button. Subsequently, there is a transition to step 5.V. If it was established in step 5.III that no storage command SPS was triggered, which is denoted by "n" in FIG. 5, there is a direct transition to step 5.V, without carrying out step 5.IV beforehand.

In step 5.V there is a query as to whether an occupied virtual storage button BST was actuated. If this is the case, which is denoted by "y" in FIG. 5, there is a transition to step 5.VI. If no virtual storage button BST was actuated, which is denoted by "n" in FIG. 5, there is a return to step 5.II. In step 5.VI, a device position POS assigned to the actuated virtual storage button BST is displayed. Subsequently, there is a query in step 5.VII as to whether a control command ST for actuating the recalled device position POS was triggered, for example with the aid of an additional hand switch 5. If this is the case, which is denoted by "y" in FIG. 5, there is a transition to step 5.VIII. However, if no control command ST for actuating the recalled device position POS was triggered, which is denoted by "n" in FIG. 5, there is a return to step 5.II. In step 5.VIII, the imaging biomedical engineering device, e.g. a C-arm device, is driven into the recalled device position POS. Optionally, the displacement is made depending on the hand switch 5 being held pressed down such that an unsupervised and unintended change in position of the biomedical engineering device is prevented.

In this specific exemplary embodiment, there is subsequently a query in step 5.IX as to whether an unoccupied storage button LST is still available. Within the scope of dynamic button generation, the number of available storage buttons should be adapted to the respective requirement. If no unoccupied storage button LST is available anymore, which is denoted by "n" in FIG. 5, a new unoccupied virtual storage button LST is generated in step 5.X. If at least one unoccupied storage button LST is still available, which is denoted by "y" in FIG. 5, there is a transition to step 5.II. After a new unoccupied virtual storage button LST has been generated in step 5.X, there likewise is a transition to step 5.II.

In this way, a more flexible and user-friendly storage of device positions is achieved in comparison with conventional procedures. Specifically, there is an improvement in the storage and the retrieval of stored device positions with the aid of a dynamically adaptable visualization of the stored device positions.

Finally, reference is once again made to the fact that the devices and methods described above are merely preferred exemplary embodiments of the invention and that the invention can be varied by a person skilled in the art within the extent predetermined by the claims, without departing from the scope of the invention. For example, the storage apparatus and the method were primarily explained on the basis of the application to a C-arm system. However, the invention is not restricted to an application to C-arm systems. Rather, it can also be applied to other imaging systems. Moreover, the invention is not restricted to the biomedical engineering sector either; rather, it can, as a matter of principle, also be applied to systems for recording images for different purposes, for example for material testing or the like. For the sake of completeness, reference is also made to the fact that the use of the indefinite article "a" or "an" does not preclude the relevant features from being able to be present a number of times. Likewise, the term "unit" does not preclude the latter from consisting of a plurality of components which may optionally also be distributed in space.

The following is a summary list of reference numerals and the corresponding structure used in the above description of the invention:

1 Imaging biomedical engineering system
2 X-ray C-arm
3 Motor
4 Control unit
5 Operating switch
6 Storage apparatus
7 Storage command button
8 3D camera
12 X-ray radiation source
14 X-ray radiation detector
18 Patient table
20 Patient
26 Keyboard
30 Screens
61 Touchscreen
62 Display field
81, 82, 88 Virtual storage buttons
89 Storage button display field
Ang Angular
BST Occupied virtual storage button
Hor Horizontal
LST Unoccupied virtual storage button
POS Recording positions of the C-arm device
Orb Orbital
SPS Storage command
ST Control command
Sw Rotation about the vertical axis
Vert Displacement in the vertical direction

The invention claimed is:

1. A storage apparatus for dynamically storing and recalling a position of an imaging biomedical engineering device, the storage apparatus comprising:
   an interface to a position establishment apparatus of the imaging biomedical engineering device, configured to receive position data from the position establishment apparatus;
   a display unit with a display field, having a user interface with a plurality of virtual storage buttons which are actuatable by way of a pointer object;
   wherein:
   if an unoccupied virtual storage button which does not yet have a medical device position assigned thereto is actuated, the given storage button is assigned a current medical device position, representing a current position of the biomedical engineering device; and
   if an occupied virtual storage button which already has a medical device position assigned thereto is actuated, the stored medical device position is selected and visualized on the display field.

2. The storage apparatus according to claim 1, wherein the occupied virtual storage buttons are configured to display a screenshot of the respectively stored medical device position and/or the screenshot imaged in accordance with a fully synchronous 3D model of the installation in accordance with an actual position of the medical device and/or a dynamic recording of screenshots for device position visualization and filing of the screenshots on the respective storage button.

3. The storage apparatus according to claim 1, wherein said user interface includes a virtual delete button configured to be actuated by way of a pointer object, for deleting a currently assigned medical device position.

4. The storage apparatus according to claim 3, wherein a given storage button is dragged onto the delete button by way of the pointer object and dropped there, whereupon the medical device position assigned to the given storage button is deleted and a corresponding screenshot is removed.

5. The storage apparatus according to claim 1, wherein said user interface has a virtual storage command button and the storage apparatus is configured only to store a current medical device position if said storage command button is also actuated in addition to the unoccupied virtual storage button.

6. The storage apparatus according to claim 1, which comprises a switch, by means of the actuation of which a control command for setting a medical device to a selected stored medical device position is generated after selecting a virtual storage button which has assigned to it a stored medical device position.

7. The storage apparatus according to claim 1, wherein the virtual storage buttons have a selection function and, additionally, a storage function or a control function for controlling the setting of a medical device position depending on an actuation time thereof.

8. The storage apparatus according to claim 7, wherein the selection function of a virtual storage button is triggered in the case of a relatively short actuation of the virtual storage button and the storage function or the control function is triggered in the case of a relatively longer actuation of the virtual storage button.

9. The storage apparatus according to claim 1, wherein some of said virtual storage buttons are configured to store device positions predefined in advance and/or the predefined device positions comprise a transport position and a zero-point position.

10. A biomedical engineering imaging system, comprising an adjustable image-recording unit and a storage apparatus according to claim 1 connected to said image recording unit.

11. The biomedical engineering imaging system according to claim 10, further comprising a setting switch configured to output a control signal for setting the medical device position assigned to an occupied virtual storage button after selecting the occupied virtual storage button and after additional actuation of said setting switch.

12. The biomedical engineering imaging system according to claim 11, wherein said setting switch comprises a hand switch or a foot switch configured to output the control signal only during a period of time when said setting switch is actuated.

13. The biomedical engineering imaging system according to claim 12, comprising a 3D camera configured to record real volume data including a user position, which are taken into account when creating a 3D model.

14. The biomedical engineering imaging system according to claim 10, comprising a C-arm system.

15. A method for dynamically storing and for recalling medical device positions of a biomedical engineering imaging system, the method comprising:

providing a storage apparatus with a display unit having a display field with a user interface, the user interface including a plurality of virtual storage buttons;

actuating a virtual storage button;

if an unoccupied virtual storage button which does not yet have a medical device position assigned thereto is actuated, storing a current medical device position in assignment to the respectively actuated storage button; and if an occupied virtual storage button which already has a medical device position assigned thereto is actuated, selecting the stored medical device position and visualizing the position on the display field.

16. A computer program product, which is loadable from a non-transitory computer readable medium directly into a memory of a programmable storage apparatus, with program code sections for carrying out the steps of the method according to claim 15, when the program is executed in the storage apparatus.

* * * * *